(12) United States Patent
Simpson et al.

(10) Patent No.: US 12,085,646 B2
(45) Date of Patent: Sep. 10, 2024

(54) MATRIX TRANSDUCER CONFIGURABLE AS A ONE-DIMENSIONAL TRANSDUCER IN ULTRASOUND IMAGING

(71) Applicant: Siemens Medical Solutions USA, Inc., Malvern, PA (US)

(72) Inventors: Terry E. Simpson, Sammamish, WA (US); Henry G. Pavy, Cupertino, CA (US); Robert Petersen, Issaquah, WA (US); David A. Petersen, Fall City, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 507 days.

(21) Appl. No.: 16/949,698

(22) Filed: Nov. 11, 2020

(65) Prior Publication Data

US 2022/0146669 A1 May 12, 2022

(51) Int. Cl.
*G01S 15/89* (2006.01)
*G01S 7/52* (2006.01)

(52) U.S. Cl.
CPC ...... *G01S 15/8925* (2013.01); *G01S 15/8927* (2013.01); *G01S 7/52095* (2013.01)

(58) Field of Classification Search
None
See application file for complete search history.

(56) References Cited

U.S. PATENT DOCUMENTS

| | | | |
|---|---|---|---|
| 6,183,419 B1 * | 2/2001 | Wildes | G01S 7/52046 600/447 |
| 7,635,334 B2 | 12/2009 | Phelps | |
| 7,691,063 B2 | 4/2010 | Petersen | |
| 7,794,400 B2 | 9/2010 | Phelps | |
| 7,981,039 B2 | 7/2011 | Peteresen | |
| 8,226,563 B2 | 7/2012 | Peteresen | |
| 2005/0096546 A1 * | 5/2005 | Hazard | B06B 1/0292 600/447 |
| 2005/0228277 A1 * | 10/2005 | Barnes | G01S 15/8927 600/459 |
| 2005/0243812 A1 * | 11/2005 | Phelps | G01S 7/5208 370/360 |
| 2009/0171213 A1 * | 7/2009 | Savord | G01S 7/5208 600/447 |
| 2009/0306510 A1 * | 12/2009 | Hashiba | G01S 7/52095 600/447 |
| 2010/0020645 A1 * | 1/2010 | Wodnicki | G10K 11/004 367/155 |
| 2019/0083064 A1 * | 3/2019 | Nguyen | A61B 8/54 |

FOREIGN PATENT DOCUMENTS

JP 2011050491 A * 3/2011

* cited by examiner

*Primary Examiner* — Joel Lamprecht
*Assistant Examiner* — Ashish S Jasani

(57) ABSTRACT

For ultrasound imaging using a matrix transducer, interconnects or switches are provided to allow sub-arrays forming a 1D array, such as with sub-arrays one element wide with the maximum number of elements in elevation. Where groups are used to limit the switches and available system channels per group, an extra switch may connect between elements of different groups through a group output to extend a sub-array across groups. To further limit the number of switches, the group may be sub-divided where different combinations of sub-groups are connectable with different combinations of the system channels for the group.

11 Claims, 6 Drawing Sheets

MATRIX TRANSDUCER CONFIGURABLE AS A ONE-DIMENSIONAL TRANSDUCER IN ULTRASOUND IMAGING

BACKGROUND

The present embodiments relate to ultrasound imaging with a matrix (e.g., two-dimensional (2D)) transducer (XDCR) array. An ultrasound imager may releasably connect with different ultrasound transducers, such as a one-dimensional array for 2D or planar imaging or a 2D array for three-dimensional (3D) or volume imaging. Customers prefer having a "one probe solution" in which a single transducer can be used to generate both high-quality 2D images and high-quality volume images.

Matrix transducers have a 2D acoustic array with a relatively large number of elements that are mapped and allocated to a relatively small number of system or beamformer channels. Partial beamforming may be used to combine signals from sub-arrays where one sub-array is provided for each beamformer channel. The combination of elements in sub-arrays occurs proximal to the acoustic components of the transducer to minimize wiring interconnects. The elements are grouped together within the electronics to form the sub-arrays. The forming of sub-arrays reduces the number of interconnects and system channel requirements but has a negative impact on the acoustic performance and spatial resolution.

To reduce the number of switches for routing, the sub-arrays are grouped together to form groups. The groups allow for a fixed number of system channels (e.g., four) to form sub-arrays with variable sizes and shapes for the elements within the group. U.S. Pat. No. 7,691,063 shows some embodiments of this grouping for sub-array routing to system or beamformer channels. By limiting the number of sub-arrays within a group, a corresponding limit on the number of switches per element and system channel connections per group is provided. This limit restricts the number of sub-array shapes and sizes, limiting the ability to from a 1D array using the matrix transducer. Matrix ultrasound sub-array shapes and sizes have been selected to allow acceptable imaging quality when focusing anywhere within a 3D volume while minimizing the number of system channel switches needed per element. When planar scanning for 2D imaging, the sub-array shapes and orientations are not ideal and have reduced imaging performance as compared to dedicated 1D transducers. The transducer probe may have to be switched to provide desired 2D imaging. Switching transducers during an exam may be inconvenient. Generally, sonographers have accepted the limitations that come with reduced 2D image quality in order to gain the ability to use 4D imaging modes with one transducer probe.

SUMMARY

By way of introduction, the preferred embodiments described below include systems, methods, and/or computer readable storage media for ultrasound imaging using a matrix transducer. Interconnects or switches are provided to allow sub-arrays forming a 1D array, such as with sub-arrays one element wide with the maximum number of elements in elevation. Where groups are used to limit the switches and available system channels per group, an extra switch may connect between elements of different groups through a group output to extend a sub-array across groups. To further limit the number of switches, the group may be sub-divided where different combinations of sub-groups are connectable with different combinations of the system channels for the group.

In a first aspect, a transducer system is provided for ultrasound imaging. A two-dimensional array of transducer elements is provided. Each of the transducer elements connects with five or fewer routing switches. One of the five or fewer routing switches is connectable to multiple of the transducer elements. A controller is configured to operate the routing switches to form a first set of sub-arrays of the transducer elements as a one-dimensional array and form a second set of sub-arrays of the transducer elements as a multi-dimensional array.

In a second aspect, a method is provided for using a matrix array in two-dimensional ultrasound imaging. Contiguous sets of transducer elements of the matrix array are grouped. The matrix array has a N×M arrangement of the contiguous sets where N is a number in a first direction and M is a number in a second direction perpendicular to the first direction. Each of the contiguous sets is configurable into different sub-array arrangements. One of the different sub-array arrangements forms parallel sub-arrays with greater extent in the first direction than extent in the second direction. In the one of the different sub-array arrangements, the sub-arrays between different ones of the contiguous sets are connected with a same number of M in in the second direction, the connecting creates a one-dimensional array. Ultrasound imaging is performed with the one-dimensional array.

In a third aspect, a transducer system is provided for ultrasound imaging. A two-dimensional array of transducer elements is provided. A multiplexer is configured to connect the transducer elements into a one-dimensional array where each array element of the one-dimensional array has a width of a single one of the transducer elements in azimuth and a height of multiple of the transducer elements in elevation and is configured to connect the transducer elements into a multi-dimensional array where each array element of the multi-dimensional array is formed from multiple of the transducer elements. A controller is configured to control the multiplexer to form the one-dimensional array or the multi-dimensional array.

The present invention is defined by the following claims, and nothing in this section should be taken as a limitation on those claims. The various aspects described above may be used individually or in any possible combination. Other aspects and advantages are discussed below in conjunction with the preferred embodiments. These further aspects and advantages may be used independently of any of the aspects described above.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
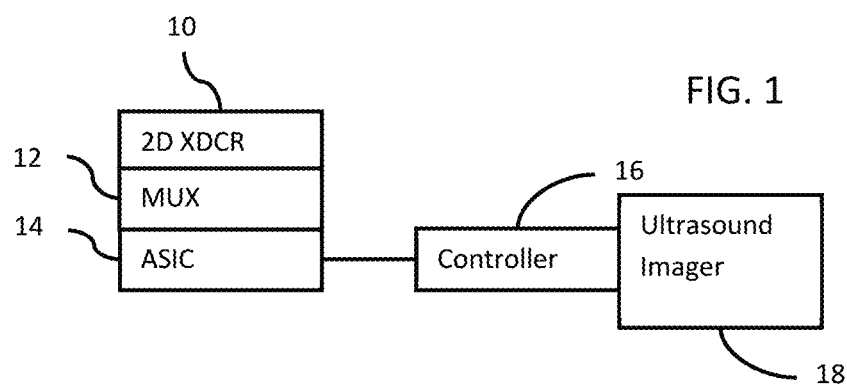
FIG. 1 is a block diagram of one embodiment of a transducer system.

A matrix transducer has configurable sub-arrays allowing for high resolution 2D imaging. Switches and routing, such as in a matrix application specific integrated circuit (ASIC) or other multiplexer, extend the reach of sub-arrays to form 1D transducer elements. The matrix sub-arrays may be used more efficiently, re-configuring the sub-arrays to support desired shapes within a grouping and, additionally, to allow for the inclusion of a sub-array shape for forming a 1D array. The sub-array definition for 2D imaging results in a 1D array formed by the matrix transducer that is comparable in size and shape to the element size and shape in a dedicated 1D transducer. The sub-array size and/or shape being similar to a 1D transducer may result in higher resolution images when scanning a plane. The ability to configure as a 1D array may allow for improved spatial resolution and image quality on par with 1D probes. One matrix transducer or probe may operate well for 2D and 3D imaging.

The sub-arrays of a matrix array may be re-configured to support various sub-array orientations including for a 1D array while limiting the number of switches per element. Groupings of elements linking different sub-arrays within a grouping to a limited number of system channels provide for a limited number of switches while allowing different sub-arrays in each grouping. One sub-array arrangement may be for 2D imaging where sub-arrays from different groups connect to a same output rather than separate outputs by group.

The switch limitation may be solved in various ways. In one approach, an additional switch per element is added in a manner that supports the sub-array orientations while adding support for an additional high resolution 2D mode (1D array), such as for scanning in a plane. The mapping of elements to potential sub-array outputs is redefined to allow for additional sub-array shapes and orientations, particularly a sub-array that is narrow in azimuth and tall in elevation like a 1D transducer. A global control and additional switches re-configure the element mapping to support narrow azimuthal and tall elevation sub-array orientation. In another approach, the groups are sub-divided so that fewer switches (e.g., 3) per element may be used to connect to the limited number (e.g., 4) of system channels per group. The elements are grouped within a grouping to allow for overlapping patterns and enable desired sub-array shapes and orientations for 3D imaging. The extra switch (e.g., 4th switch) is then used to connect elements or sub-arrays between groups for 2D imaging. Utilizing either of these approaches allows a small number of sub-array outputs to be used to support a large number of sub-array shapes and sizes. The elements are mapped to sub-array outputs to allow the inclusion of a 1D sub-array shape to improve imaging resolution in the azimuthal imaging plane. Within a group exchange, sub-array shapes for the 1D functionality avoid increasing the number of outputs required per group.

FIG. 1 shows one embodiment of a transducer system for ultrasound imaging. The transducer system is formed from a matrix array that may be reconfigured to support small azimuth spacing of effective elements for azimuth 2D imaging. One transducer may provide both 3D focused volume scanning and 2D imaging without compromising the quality of the 2D imaging.

Figure 11:
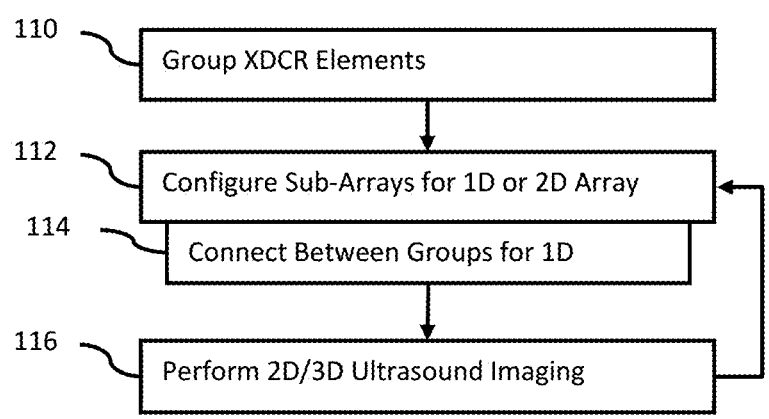
FIG. 11 is a flow chart diagram of one embodiment of a method for using a matrix array in two-dimensional ultrasound imaging.

The transducer system implements the method of FIG. 11 or other methods. Routing switches configure sub-arrays for 3D and 2D imaging, allowing one 2D transducer 10 to be used as a 2D array or a 1D array.

The transducer system includes a 2D transducer (XDCR) 10, a multiplexer 12, an application specific integrated circuit (ASIC) 14, a controller 16, and an ultrasound imager 18. Additional, different, or fewer components may be provided. For example, the multiplexer 12 is integrated within and/or provided as part of the ASIC 14. As another example, the ASIC 14 is not provided or is integrated as part of the controller 16. In yet another example, the transducer system does not include the ultrasound imager 18 and/or controller 16.

The matrix transducer 10 is a 2D array of transducer elements. The transducer elements are piezoelectric, CMUT, or PMUT elements. The elements are distributed in a fully sampled Cartesian grid as a 2D transducer array. Sparse sampling or other grid spacings of elements may be provided. Any number of elements may be provided, such as hundreds or thousands.

Figure 2:
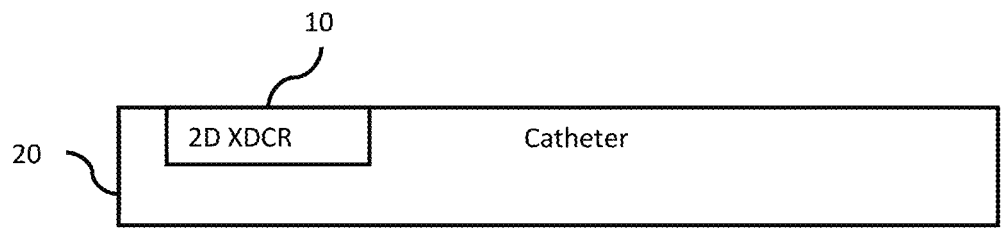
FIG. 2 is a block diagram of one embodiment of a transducer of the transducer system of FIG. 1 in a catheter.

In one embodiment, the array of elements is positioned within a detachable transducer assembly. In one embodiment, the transducer 10 is housed in a hand-held transducer housing. Alternatively, a catheter or endoscope configuration is used. FIG. 2 shows an example where the transducer 10 is in catheter, such as a catheter having a diameter of 12-14 french. The transducer 10 is part of a matrix intra-cardiac echography transducer probe. For cardiac imaging from a catheter, volume imaging is desirable. High resolution images comparable to existing catheters with dedicated 1D transducers arrays is also desired for structural heart procedures.

The 2D array may have equal or unequal number of elements distributed in azimuth and elevation. For example, the two-dimensional array of the transducer elements has a greater number of the transducer elements along azimuth than a lesser number of the transducer elements along elevation. In one embodiment, the 2D array is 24 elements in elevation and 72 elements in azimuth. Square, rectangular, circular, triangular, hexagonal, or other shaped arrays may be used.

Figure 3:
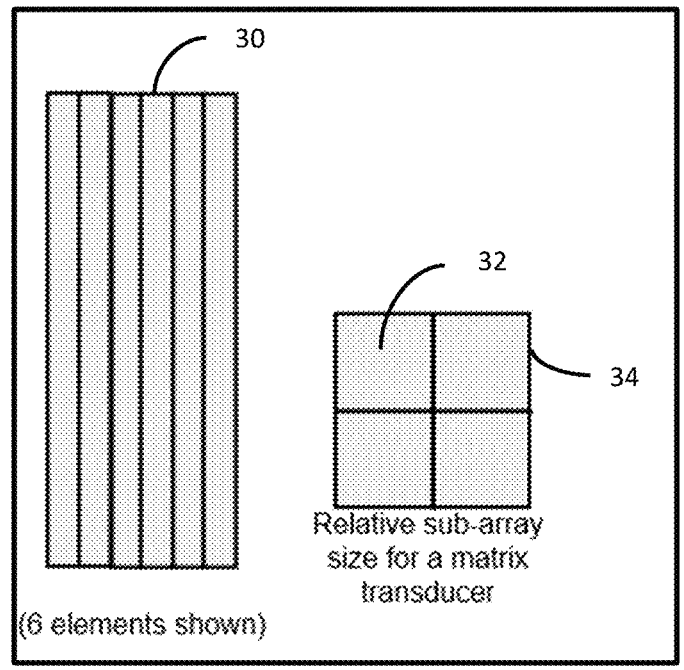
FIG. 3 illustrates a comparison of part of an example 1D array with part of an example 2D array.
Figure 4:
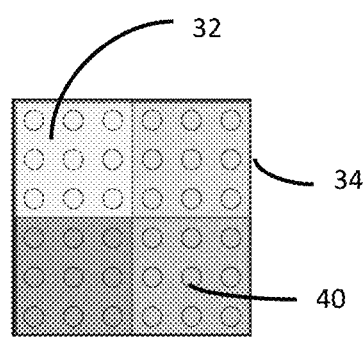
FIG. 4 illustrates an example grouping of transducer elements.

FIG. 3 shows an example comparison of part of a 1D array to part of a 2D array formed by the transducer 10. The horizontal direction is shown as "azimuth" while the vertical direction is shown as "elevation." 1D transducers and catheters typically use elements that are relatively narrow in the azimuth dimension and wide in the elevation dimension. The left side of FIG. 3 shows part of a 1D array of elements 30, which elements are 146 μm in width (azimuthal pitch) and 2.2 mm in height (elevation). Other sizes may be provided. The elements 30 have relatively small element sizes in the direction of focus (azimuth) which improves spatial resolution. The right side of FIG. 3 and FIG. 4 shows part of a matrix or 2D array. A group 34 of, for example, thirty-six elements 40 is shown. The elements 40 may be 146 μm×146 μm each. Other shapes or sizes may be used. The group 34 is divisible into four sub-apertures or sub-arrays 32. Each sub-array 32 forms an effective element from the perspective of the ultrasound imager 18 or beamformer. The four sub-arrays 32 are formed from square arrangements of nine elements 40 in this example (e.g., four squares of FIG. 3 or the four boxes with different shading of FIG. 4). Matrix arrays typically support square or rectangular sub-arrays, which are good for performing volume imaging, but are relatively poor at generating high quality 2D images comparable to 1D transducers.

In the example of FIG. 4, each group 34 is made up of thirty-six elements 40, six elements 40 in azimuth by six elements 40 in elevation. Other numbers of elements 40 may be provided, including non-square arrangements. Each of the elements 40 within a group 34 is mappable to outputs for four sub-arrays 32 that drive a respective four system channels. This control uses four switches for each element 40 and four sub-array outputs routable to each element 40.

Figure 8A:
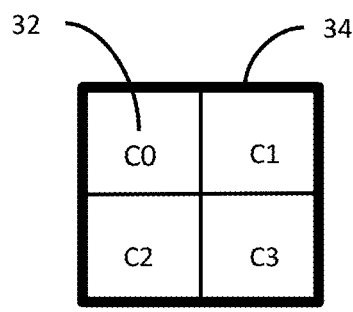
FIGS. 8A-D show example sub-array arrangements in an example grouping.
Figure 8B:
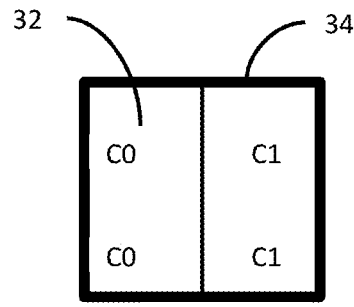
Figure 8C:
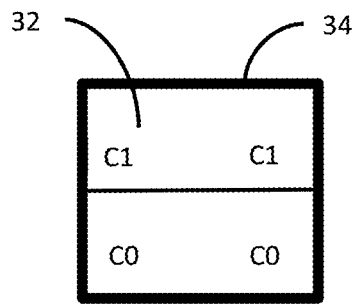

The sub-arrays 32 may be configurable, such as providing two, three, or four sub-arrays 32 for a given group 34 (see FIGS. 8A-C). The groupings of the matrix transducer 10 define elements 40 through switching that can be controlled together to connect to specific system channels. For example in the 24×72 element 40 transducer 10, ninety-six system or beamformer channels connect to a respective twenty-four groups, where four system channels are assigned to each group and each group may form up to four sub-arrays 32.

To limit the number of routing switches, the elements 40 of the transducer 10 may be divided into or assigned to groups 34. The elements 40 are separated into groups 34 where each element 40 is in one group 34. Any number of groups 34 may be provided. Within each group 34, different sub-arrays 32 of elements 40 may be formed. Each sub-array 32 connects to an output to a system or beamformer channel for imaging. Each group 34 may have a given number of system or beamformer channels assigned, such as having four outputs from each group 34 for connecting with a respective four system or beamformer channels. Four or fewer sub-arrays 32 are formed by the elements 40 of a group 34 to connect with a respective four or fewer system channels. Sub-arrays 32 of different groups 34 connect to different channels.

Figure 5:
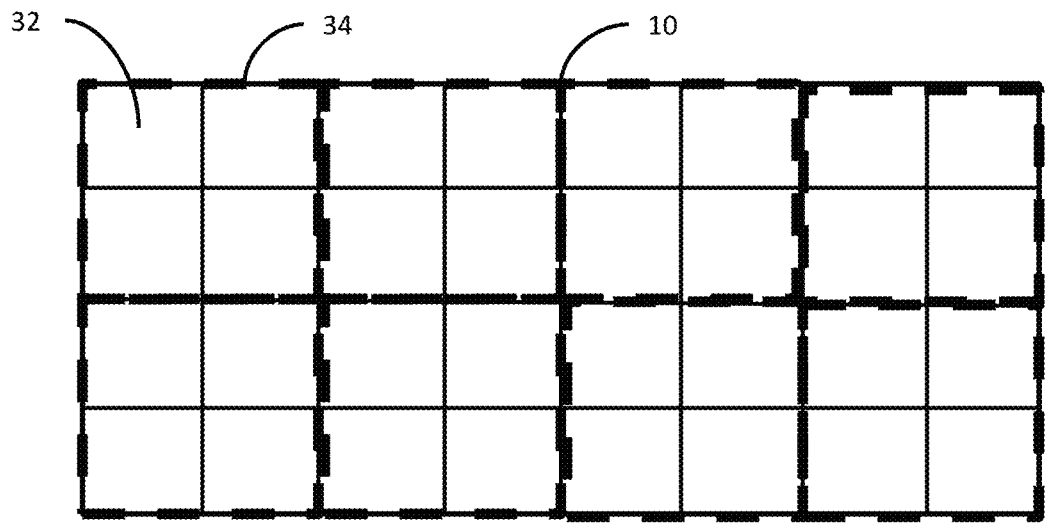
FIG. 5 illustrates a matrix transducer array configured as a 2D array with an example grouping in one embodiment.

FIG. 5 shows an example transducer 10 with eight groups 34 where each group 34 (dashed lines) is configured by switching to form four square sub-arrays 32. Other number of groups 24, numbers of sub-arrays 32 per group 34, shapes of the transducer 10, shapes of the groups 34, and/or shapes of the sub-arrays 32 may be used. Each square or sub-array 32 represents one effective element from the perspective of the beamformer of the imager 18. Signals from the elements 40 of the same sub-array 32 are provided to the one system or beamformer channel. For example, thirty-two system channels connect with the thirty-two sub-arrays 32 of FIG. 5.

Figure 6:
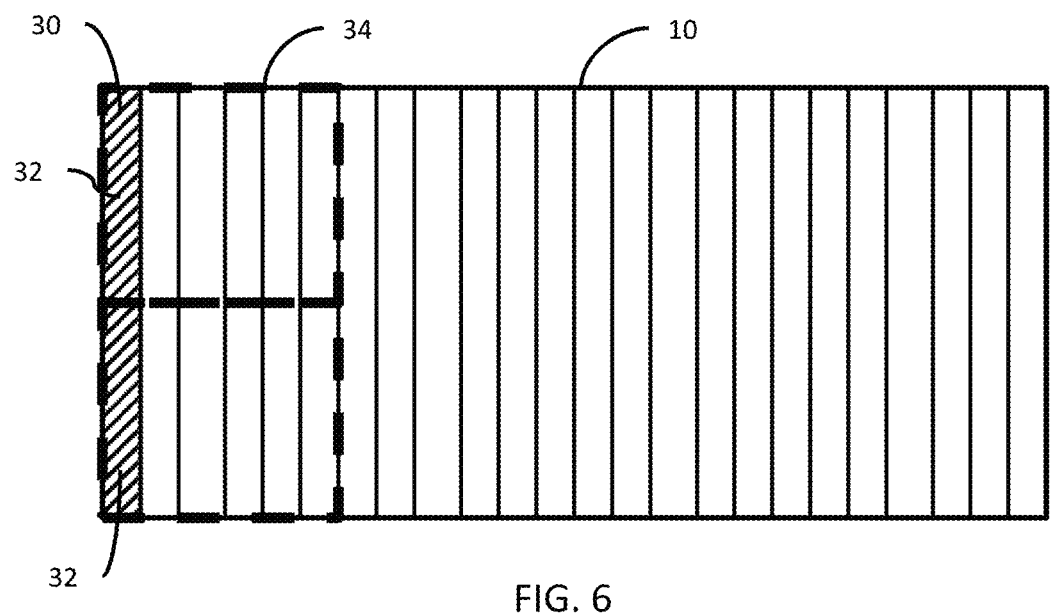
FIG. 6 illustrates a matrix transducer array configured as a 1D array with an example grouping in one embodiment.
Figure 7:
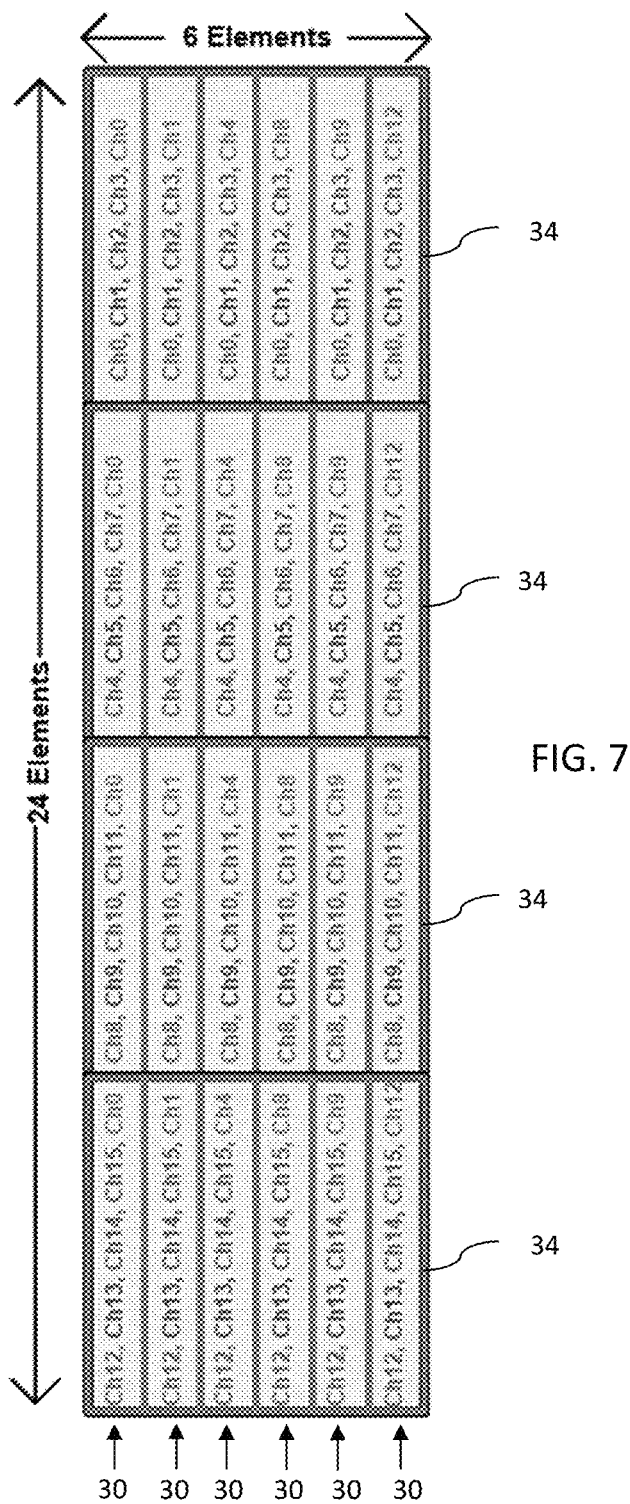
FIG. 7 shows part of a matrix transducer array configured as a 1D array with channel connections for the different groups according to an embodiment.

FIG. 6 shows the example matrix transducer 10 with eight groups 34 (only two shown) configured as a 1D array of elements 30 (only one highlighted with diagonal lines). The elements 30 are formed from sub-arrays 32 of different groups 34 connected together (i.e., the element 30 crosses the groups 34 in elevation to provide a greater elevation extent). In the example where each group 34 is 6×6 elements 40 (see FIG. 4), the array element 30 (formed by sub-arrays 32 in the two different groups 34) is one element 40 wide in azimuth and 12 elements high in elevation. Wider (e.g., two elements 40) in azimuth and/or shorter (e.g., less than all elements 40) in elevation may be used to form the 1D array of elements 30. FIG. 7 shows the elements 30 formed from sub-arrays 32 across four groups in elevation, providing a 1×24 elements 40 to form the 1D array of elements 30. This 1D array of FIG. 6 is desired for 2D imaging and models the 1D array of FIG. 3.

Switches of the multiplexer 12 configure the matrix transducer 10 to provide the desired arrangement of sub-arrays 32. Given an unlimited number of routing switches, any element 40 may connect with any system channel. The groupings 34 allow for a limited number of switches to form sub-arrays 32 and connect with system channels. The physical, hardware, or fixed connections of the switches define the groups 34. For example, within a group 34, switches are fixedly connected to elements 40 and particular outputs of the group 34 for a limited selection of system channels (e.g., four system channels for each group 34). The configuration of the sub-arrays 32 and connections to system channels is performed through software and/or firmware controls of the multiplexer 12 (i.e., opening and closing different switches per element 40).

The multiplexer 12 forms a plurality of routing switches. The switches are transistors but may be other types of switches. In alternative embodiments, the switches are provided without a separate multiplexer 12. The multiplexer 12 may be integrated with the ASIC 14 and/or the transducer 10.

Routing through backing of the transducer 10, within the multiplexer 12, within the ASIC 14, on flexible circuit material, with wire bonding, through solder bumps, and/or other conductors connects the switches to the transducer 10 and the ASIC 14, and/or beamformer of the ultrasound scanner 18. The ends of the switches are connectable or fixedly connect. The switches may be opened or closed to disconnect or connect, respectively, the components connected with the ends of the switches (i.e., to connect a given element 40 to one of the available outputs for the group 34).

Each of the transducer elements 40 connects with five or fewer routing switches of the multiplexer 12. The other side of the switches connects to beamformer channels of the ultrasound imager 18 and/or transducer elements 40 in other groups. The connection may be direct or indirect. For example, a switch with an element 40 in a group 34 connects with a partial beamformer channel of the ASIC 14. One switch for each or a sub-set of other elements 40 of the same group 34 connects with other partial beamformer channels of the ASIC 14 for summation, delay and sum, and/or phase and sum to create a partially beamformed signal for the sub-array 32. The output of the partial beamformer is an output for the group 34 and connects with the beamformer channel of the ultrasound imager 18. Any number (e.g., four or fewer) of sub-arrays 32 for the same group 34 uses a respective number of switches connected to the elements 40 of that group 34 to connect with a respective number of channels of the beamformer of the ultrasound imager 18. Similar arrangements are provided for other groups 34 to connect with other outputs of the groups 34 for providing signals to different channels of the beamformer of the ultrasound imager 18.

The switches may be configured to connect the transducer elements 40 into a multi-dimensional array, such as shown in FIG. 5. Each array element (sub-array 32) of the multi-dimensional array is formed from multiple of the transducer elements 40. In the example of FIG. 5, each group 34 has four sub-arrays 32 where each sub-array 32 is formed from nine elements 40. The switches for the elements 40 connect the elements 40 to the desired beamformer channel of the ultrasound imager 18. For each group 34, four switches per element 40 allow selection of the four respective outputs to four respective beamformer channels. The elements 40 of one sub-array 32 use switches to connect with the same output to the beamformer channel. The different sub-arrays 32 connect with different respective outputs to the beamformer channels of the ultrasound imager 18. By closing different switches per element 40, sub-arrays 32 of different sizes, shapes, orientations, and/or numbers may be formed and connected with respective beamformer channels of the ultrasound imager 18.

One switch per element 40 may connect from the element 40 to another group 34, providing a connection between elements 40 of different groups 34. This connection may be direct or indirect through connection to an output to a beamformer channel. All elements 40 include such a switch. Alternatively, just the elements 40 bordering the group 34 or fewer than all the elements 40 include a switch for connecting between elements of groups 34. The multiplexer 12 is configured to connect the transducer elements 40 into a 1D array using these switches, so at least one element 40 of each sub-array 32 is connectable through a switch to at least one element 40 of another sub-array 32 to form the effective or 1D array of elements 30 (see FIG. 6). Switches of the other elements 40 connect to other elements 40 in the sub-array 32 of the group 34 or also connect to elements 40 of the sub-array 32 of the other group 34. The connections allow configuration where each array element 30 of the 1D array has a width of one of the transducer elements 40 in azimuth and a height of multiple of the transducer elements 40 in elevation, forming the effective or 1D array of elements 30. In the example of FIG. 6, the sub-array 32 of one group 34 connects with the sub-array 32 of the other group 34 through one or more switches of the multiplexer 12 to a same output, forming the array element 30.

Figure 9:
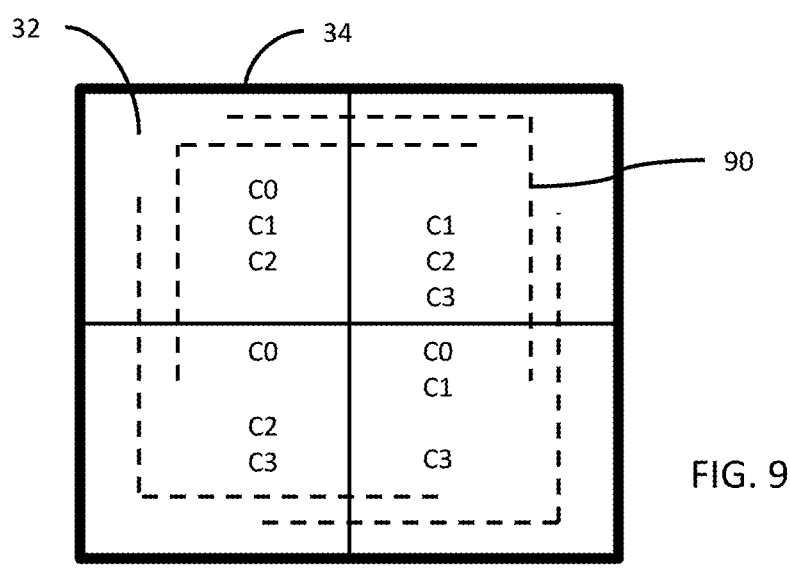
FIG. 9 shows example switch reduction through sub-division of a grouping.

FIGS. 7 and 9 show two embodiments of arrangement or assignments of switch connections to allow configuration of both a 1D array and a 2D array for 2D imaging and 3D imaging, respectively. FIG. 7 is directed to an embodiment adding a switch for element 40-to-element 40 connection between groups 34 while maintaining the switches (e.g., four switches) for configuring sub-arrays 32 of different shapes for the 2D array. The extra switch per element 40 allows connection to outputs of a different group 34 for across group element connection. FIG. 9 is directed to an embodiment adding a switch for connection between groups 34 while reducing the number of switches for forming different sub-arrays 32 so that a fewer number of total switches is provided per element 40.

In the embodiment of FIG. 7, the multiplexer 12 has five or fewer switches per element 40. Greater or fewer numbers of switches per element 40 may be provided, such as two or fewer where only one switch allows selection between two beamformer channels for two sub-arrays 32, for the 2D array configurations. Six switches could be used to allow a 1D array to be defined at any angle on the 2D array rather than just along elevation or azimuth.

Five or fewer switches allows for four different sub-arrays 32 in a group 34 where one switch per element 40 is for group 34-to-group 34 connection. A remaining four or fewer of the switches are for connecting to outputs of the group 34, which outputs connect or are connectable to beamformer channels of an imaging system 18. In aggregate for the 2D array, the routing switches (e.g., four or fewer per element 40) form a repeating pattern of sub-arrays 32 across the transducer 10 by group 34. The same shape and orientation of sub-arrays 32 as effective elements of the 2D array use switches to connect the sub-arrays 32 to different system channels of the beamformer of the ultrasound imager 18. One of the switches (e.g., one of the five or fewer switches per element 40) is for connecting between the transducer elements 40 in the 1D array configuration. Through this group 34-to-group 34 (i.e., sub-array 32-to-sub-array 32 and/or element 40-to-element 40 via common output) switch, a given element 40 connects to the elements 40 of the same sub-array 32 and to elements of the sub-array 32 of one or more other groups 34 to form the effective element 30.

When the 1D array is to be formed by the matrix transducer 10, the switches for group 34-to-group 34 connection of respective sub-arrays 32 is closed. Some of the switches for group 34-to-group 34 connection may be open depending on the size of the 1D array being formed and/or whether other switches for a given sub-array 32 connect to other sub-arrays 32. When the 2D array is to be formed, the switches for group 34-to-group 34 connection are open or disconnected. Alternatively, a sub-array 32 may be formed across groups 34 (i.e., from elements 40 from different groups 34) using the switches for group 34-to-group 34 connection.

FIG. 7 shows one embodiment of switch configuration to connect to the outputs of the groups 34. Four groups 34 are shown oriented in the elevation direction. Other groups 34 may be provided along an azimuth extent. For example, the transducer 10 has twelve groups spaced in azimuth (e.g., twelve by four) for 24 elements in elevation and 72 elements in azimuth. Additional or fewer groups 34 may be provided in elevation. By providing five instead of four switches per element 40, the number of sub-array 32 outputs (i.e., outputs of the group 34) available to each group 34 extends the possibilities for the organization of the elements 40. The additional switches and sub-array outputs allow for configurable sub-array shapes within a group 34 to support focusing for volume imaging and adds the ability to re-configure the sub-array shapes to allow for high-resolution azimuthal scanning for 2D imaging.

FIG. 7 shows five output channels per group, listed as ChX. For the upper most group 34, channels Ch0-3 are four outputs used to form sub-arrays in a 2D array. Channels 0, 1, 4, 8, 9, and 12 may be used as group 34-to-group 34 connections where the elements 40 of the sub-arrays 32 have respective switches arranged to connect to those respective channels (i.e., a given element 40 has one switch to connect to one of the group-to-group channels). Each element 40 for an 1D array of elements 30 connects to the same output channel (e.g., Ch0 for the left most column of elements 40 across groups 34).

For volume imaging, the first four sub-array outputs (e.g., Ch0-3 in the upper most group 34) in each of the groups can be used to configure any sub-array shape within each group 34. For forming the 1D array for high-resolution azimuthal scanning, each column of groups 34 share and re-use six common sub-array outputs (e.g., Ch0, 1, 4, 8, 9, and 12) for group 34-to-group 34 connection of sub-arrays 32, allowing receive signals from elements 40 within a group 34 to be summed or combined together with elements 40 from other groups 34 in the same column. In the example of FIG. 7, all the elements 40 in the left most column of elements 40 connect to channel 0, forming the 1D array of elements 30 from the sub-arrays 32 of each group 34. In this example where each group 34 has six elements 40 in azimuth, six channels (Ch0, 1, 4, 8, 9, and 12) are used to form six separate array elements 30. Fewer channels may be used to form a 1D array of elements 30 and/or to form an array two or more elements 40 wide in azimuth. Other arrangements may be provided, such as using different channel assignments.

In other embodiments, the 1D array of elements 30 may be sub-divided, such as connecting the sub-arrays 32 of two groups 34 (e.g., upper two or middle two) separately from the sub-arrays 32 of two other groups 34 (e.g., lower two or outer two), forming two elements along the length of one element of a 1D array of elements 30. For example, two system channels are available to support one column of elements 40. The top half of the elements connect to one channel and the bottom half of elements connect to the other channel. Alternatively, the middle elements connect to one channel, and the outer elements connect to the other channel.

The switches used for group-to-group connection both connect across groups 34 as well as connect to the beamformer channels of the ultrasound imager 18. For example, ch0 and 1 are typically used in the upper most group 34 for connection to beamformer channels. All the elements 40 in the respective 1D array of elements 30 connected to these output channels connect to each other and to the respective beamformer channel. In the embodiment of FIG. 7, two outputs from the upper most group 34 (e.g., ch0-1), one output from the lower most group 34 (e.g., ch 12), one output from the upper middle group 34 (e.g., ch 4), and two outputs from the lower middle group 34 (e.g., ch 8-9) are used to connect the six array elements 30 to a respective six beamformer channels.

To further limit the number of switches per element 40, the embodiment of FIG. 9 may be used. The reduction in switches is provided by an arrangement for forming sub-arrays 32 for the 2D array. One switch per element 40 is provided to form the 1D array as described above for FIG. 7. Instead of four switches per element 40 for forming the sub-arrays 32 for the 2D array, a remaining three or fewer switches per element 40 are provided for connecting to outputs to beamformer channels of an imaging system 18.

Figure 8D:
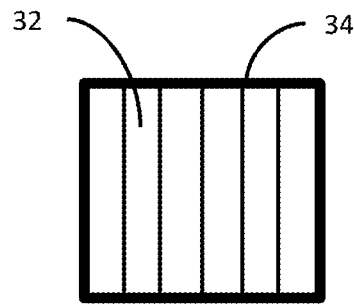

FIG. 8A-D show a group 34 with the desired sub-array sizes and shapes. FIG. 8A shows four square sub-arrays 32 using four group outputs channels C0-3. FIG. 8B shows two rectangular sub-arrays 32 in a vertical orientation using two group channels C0-1. FIG. 8C shows two rectangular sub-arrays 32 in a horizontal orientation using two group channels C0-1. FIG. 8D shows the sub-array 32 arrangement for one group 34 to form the 1D array. In the embodiment of FIG. 7, five switches per element 40 provide these four different options (i.e., four switches to connect any element to 1-of-4 sub-array outputs plus one additional switch to connect the element 40 to the sub-array output that is shared across groups). The five switches per element provide for configurating the transducer 10 into the arrays of FIGS. 8A-D. This results in each element 40 being able to switch to (Ch0, Ch1, Ch2, Ch3) plus one of the following sub-array outputs (ChA, ChB, ChC, ChD where ChA-D may be channels for other groups 34 for group 34-to-group 34 connection).

FIG. 9 shows an arrangement to support the sub-array shapes of FIGS. 8A-D with four switches per element 40 instead of five switches per element 40. Four outputs per group 34 are provided instead of the five of FIG. 7. The elements 40 within a group 34 are further sub-divided. Sub-groups 90 (see dashed line designating the quadrants for each sub-group) are formed. In the embodiment of FIG. 9, the sub-groups are formed as elements 40 of three of the four quadrants. Other sub-grouping spatial distribution may be used. Four sub-groups 90 are formed, but other numbers of sub-groups may be used. The sets of elements 40 for each sub-group 90 may be shared with one or more other sub-groups 90. Each sub-group 90 is formed from a different set of elements 40 but overlaps with one or more other sub-group 90. In the embodiment of FIG. 9, the dashed lines designate the quadrants included in each sub-group 90. Four sub-groups 90 each made up of the elements 40 of four different combinations of the four quadrants are used.

Each overlapping sub-group has a common one of the outputs. In FIG. 9, four outputs C0-4 are still provided. Since each element 40 only has three switches for the 2D array (four total switches), each element 40 is assigned three of the four output channels by sub-group 90. For example, the elements 40 of the upper left quadrant of the group 34 have three switches connecting the elements 40 to the three output channels C0-2. The elements 40 of the upper right quadrant of the group 34 have three switches each connecting the elements 40 to the three output channels C1-3. The elements 40 of the lower left quadrant of the group 34 have three switches each connecting the elements 40 to the three output channels C0, 2-3. The elements 40 of the lower right quadrant of the group 34 have three switches each connecting the elements 40 to the three output channels C0-1, 3. Each of the sub-groups are connectable with three of the four outputs per group 34. Each of the four outputs C0-3 are connectable with a different combination of three of the sub-groups.

The desired sub-array sizes and orientations (see FIGS. 8A-C) are retained while keeping the number of group outputs constant at four. By organizing the elements 40 into overlapping L-shaped groups of three quadrants, every element in an L-sub-group share one common sub-array connection with every other element in that L-sub-group. Each group 34 contains L-sub-groups that are rotated 90 degrees from each other, creating overlapping L-sub-groups 90. By connecting the appropriate sub-array outputs to each L-sub-group 90, the 3×3, 3×6, 6×3 and high-resolution azimuthal modes (see FIGS. 8A-D) are supported while not increasing the number of sub-array connections required per element 40 past four. Other sub-group shapes or arrangements may be used. Fewer switches per element may be provided, such as by using three sub-groups instead of four. A greater number of switches per element 40 may be used with sub-groups, allowing for a greater range of sub-array shapes, sizes, and/or orientations to be provided.

Referring again to FIG. 1, the ASIC 14 provides for any signal processing, such as preamplification and/or digitization. The ASIC 14 may implement control functions and/or pulsers. In one embodiment, the ASIC 14 is a partial beamformer. The signals from separate elements 40 within a sub-array are combined to provide a sub-array signal as a group 34 output channel. Delay and sum, sum, and/or phase and sum partial beamformation may be provided for each sub-array 32, resulting in signals or data for each channel of the beamformer of the ultrasound imager 18. This partial beamformer is a sub-array beamformer that beamforms separately for each sub-array 32 to provide signals for each effective element (sub-array 32 or 1D element 30) to the imager 18. The partially beamformed data is output to the system channels. From the perspective of the ultrasound imager 18, an entire sub-array 32 represents a single array element because all receive signals for all elements within a sub-array are beamformed or combined before being forwarded to the imager 18. The system will beamform the multitude of sub-array signals together.

The controller 16 is a processor, such as field-programmable gate array, ASIC, general processor, or control processor. The controller 16 controls the multiplexer 12 and/or ASIC 14. The controller 16 may control partial beamforming, such as configuring the delays or phasing to use and/or turning off partial beamforming where the signals from different elements 40 combined without phasing or delay. The controller 16 is positioned in a connector of the transducer probe, such as the connector for releasable connection with the ultrasound imager 18. In other embodiments, the controller 16 is in the ultrasound imager 18, in the ASIC 14, and/or in the probe head with the transducer 10.

Software, firmware, and/or hardware configure the controller 16 to operate the switches of the multiplexer 12. The controller 16 controls the switches to provide or utilize the desired sub-array shapes and sizes. The multiplexer 12 is controlled to form the 1D array or the 2D array. The routing switches are operated (opened or closed) to form sub-arrays 32 of the transducer elements 40 as a 1D array of elements 30 (see FIG. 6 as an example) or form sub-arrays 32 of the transducer elements 40 as a multi-dimensional array (e.g., 2D array of FIG. 5 as an example). FIG. 8A shows the sub-arrays 32 for each group 34 to form the array of FIG. 5 as a 2D array. The sub-arrays 32 for each group of FIG. 8B or 8C may be used instead for the 2D array. For the 1D array, each 1D array of elements 30 is only one element wide in azimuth and uses the full elevation extent of array of elements 40 for maximum resolution in 2D imaging. Each 1D array of elements 30 is formed from two or more sub-arrays 32 from a respective two or more groups 34. Other 1D array of elements 30 may be used where wider azimuth (e.g., two elements wide) and/or lesser elevation (e.g., fewer than all elements 40 in elevation) are used.

The ultrasound imager 18 is a medical diagnostic ultrasound imaging system. Transmit and receive beamformers connect through a transmit receive switching system to a connector for connection with a connector of an ultrasound probe. The receive beamformer beamforms the signals from the sub-arrays 32 and outputs the beamformed data to an image former, such as a detector and scan converter. A three-dimensional renderer may be provided for volume (i.e., 3D) or four-dimensional imaging. A display displays the image resulting from an acoustic scan of the patient by the transducer 10. The quality of the image is impacted by the array used to scan. By providing a 1D array with relative long elevation extent and relatively narrow azimuth extend for each array element, 2D imaging with high quality is provided. That same transducer 10 may be configured for volume imaging of the interior of the patient on the display.

Figure 10:
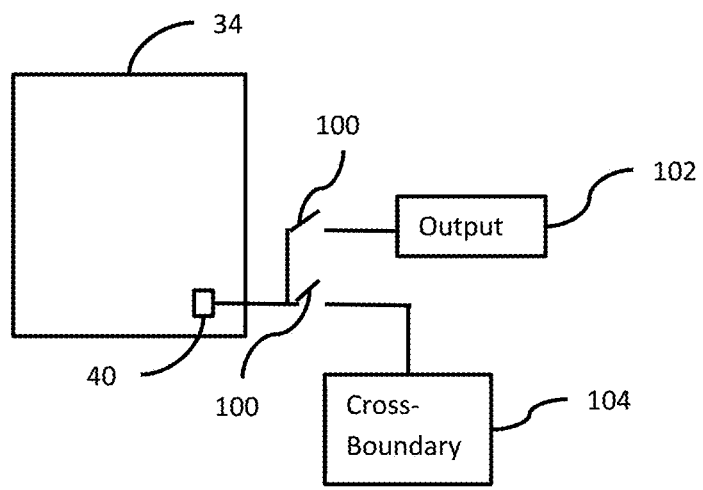
FIG. 10 shows an example embodiment using just two switches per element.

FIG. 10 shows another embodiment of a group 34 with switches 100. Only two switches 100 are provided for each element 40 of the group 34. FIG. 10 shows two switches 100 for one element 40 for simplicity. Each of the other elements 40 in the group also has two switches 100. This arrangement uses the elements 40 of the group 34 with a fixed sub-array 32 shape for use in a 2D array (i.e., all of the elements 40 of the group 34 connect to one output 102 (e.g., system channel or output of a partial beamformer). One switch 100 is used to connect the element 40 to the output 102, such as to an input to a partial beamformer that combines signals from all of the elements 40 of the group 34 for output 102 of the system beamformer channel. The other switch 104 connects the element 40 to one or more elements of one or more other groups (i.e., cross-boundary to another sub-array 32). One or both switches 100 may open or closed at a same time for imaging.

M outputs and N switches are provided in various embodiments, where N>M and the M switches connect elements to outputs within a 2D boundary (group) and the N-M extra switches connect across these boundaries. For example, a 1+2 configuration is provided where there are no groups, just fixed sub-arrays with a single dedicated output each but with two extra switches per element to allow vertical connections across boundaries to make the 1D elements for imaging. Any number (e.g., 1 or 2) extra switches per element provide long-skinny-elements for 1D imaging with or without groups 34.

FIG. 11 is a flow chart diagram of one embodiment of a method for using a matrix array in 2D ultrasound imaging. The same matrix array may be used for 3D (or 4D) imaging. Rather than using the 2D array configuration of the matrix array for 2D imaging, the matrix array is configured as a 1D array with narrow (e.g., one element wide) azimuth and long (e.g., entire elevation extent) elevation array elements or effective elements.

The method is implemented by the systems of FIG. 1 or 2, or another system. For example, the transducer 10, multiplexer 12, and/or ASIC 14 by design groups elements. The controller 16 controls the multiplexer 12 to connect the elements within groups to form the desired sub-arrays 32. The transducer 10, ASIC 14, and ultrasound imager 18 perform ultrasound imaging with the sub-arrays 32 formed by the connections. The connections may be redone to form and use other arrays. Other devices may perform any of the acts.

Additional, different, or fewer acts may be provided. For example, act 114 is not performed where the transducer is configured as a 2D array. In another example, act 116 is not performed as imaging but to create an image or scan data without display. Acts for configurating the ultrasound imager 18 and/or controller 16 may be provided. The acts are performed in the order shown (top to bottom or numerical) or another order.

In act 110, the design of the transducer 10 and multiplexer 12 groups contiguous sets of transducer elements 40 of the matrix array. Each group of contiguous sets of elements 40 forms a group 34. The matrix array has a N×M arrangement of the contiguous sets where N is a number in elevation and M is a number in azimuth, such as 4×12. Each of the contiguous sets is configurable into different sub-array arrangements, such as shown in FIG. 8A-D. One of the different sub-array arrangements forms parallel sub-arrays (see FIG. 8D) with greater elevation extent than azimuth extent.

For each contiguous set, a limited number of outputs for connecting with a respective number of beamformer channels of the imager 18 are provided. For example, four or fewer outputs are provided. Another output may be provided for group-to-group connection as well as connection with a beamformer channel.

In act 112, the controller configures the sub-arrays within each of the contiguous sets of elements 40. The configuration provides the desired arrangement of sub-arrays, such as one of the arrangements of FIGS. 8A-C for 3D imaging or the arrangement of FIG. 8D for 2D imaging. The arrow from act 116 to act 112 shows repetition for use of a different configuration of the array. The sub-arrays are configured to provide a multi-dimensional sub-array arrangement or a 1D sub-array arrangement.

In act 114, the controller uses the switches to connect the elements 40 to group outputs or channels to configure in act 112. For example, a 1D array is provided. The sub-arrays between different ones of the contiguous sets connect with the same outputs to form the 1D array of array elements 30. For full elevation extent, sub-arrays from M contiguous sets are connected. Any number of sub-arrays in each contiguous set may be used, such as six. Separate outputs are used for each of the number of sub-arrays in each continuous set to form a corresponding number of array elements 30, creating the 1D array across contiguous sets. The switches connect between contiguous sets in elevation by connecting to a same output despite being from different contiguous sets or groups 34.

As another example, the switches connect to provide 2D sub-array arrangements, such as one of the arrangements of FIGS. 8A-C. Rather than switching elements from different contiguous sets to the same output, each sub-array of each contiguous set is connected to a separate group output and corresponding system channel. The outputs of the contiguous sets are not shared between contiguous sets.

In the embodiment of FIG. 9, the switches connect to a limited number of the outputs of the contiguous set. For example, the overlapping L-shaped arrangements defined by the grouping of act 110 are used. An element 40 in any given quadrant or sub-grouping is connected with one of three of the four group outputs. This arrangement allows for any of the sub-array arrangements of FIGS. 8A-C to be formed.

In act 116, the ultrasound imager performs ultrasound imaging with the transducer as configured. For transmit operation, a transmit beamformer provides signals separately to individual actual elements or to sub-arrays. For receive operation, signal from individual elements are combined, such as by partial beamforming or connection to a common conductor. The combination is by sub-array or combination of sub-arrays in the 1D configuration. The sub-array signals from the different contiguous sets are provided through group outputs to the beamformer channels of the imaging system. The signals are beamformed and image formed to generate one or more images representing an interior of the patient.

2D imaging is performed with the configured 1D array. A planar region is scanned and imaged using the 1D arrangement of sub-arrays. 3D or 4D imaging is performed with the configured 2D array. A volume region is scanned and imaged using the 2D arrangement of sub-arrays.

While the invention has been described above by reference to various embodiments, many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A transducer system for ultrasound imaging, the transducer system comprising:
a two-dimensional array of transducer elements, each of the transducer elements connected with routing switches, wherein the transducer elements are organized into overlapping L-shaped groups across three quadrants, wherein each transducer element in a respective L-shaped group shares one common connection with every other element in the respective L-shaped group; and
a controller configured to operate the routing switches to form a first set of sub-arrays of the transducer elements as a one-dimensional array and form a second set of sub-arrays of the transducer elements as a multi-dimensional arrays.

2. The transducer system of claim 1, wherein the routing switches for the transducer elements comprise transistors in a multiplexer.

3. The transducer system of claim 1, wherein the two-dimensional array of the transducer elements has a greater number of the transducer elements along azimuth than a lesser number of the transducer elements along elevation.

4. The transducer system of claim 3, further comprising a catheter, the two-dimensional array of the transducer elements being in the catheter.

5. The transducer system of claim 3, wherein each of the sub-arrays of the first set form a single array element including only one transducer element wide in azimuth and the lesser number of transducer elements high in elevation.

6. The transducer system of claim 1, further comprising a sub-array beamformer configured to partially beamform by the sub-arrays and output partially beamformed data for each of the sub-arrays to system channels of an ultrasound imager.

7. A method for using a matrix array in two-dimensional ultrasound imaging, the method comprising:
grouping contiguous sets of transducer elements of the matrix array, the matrix array having a N×M arrangement of the contiguous sets where N is a number in a first direction and M is a number in a second direction perpendicular to the first direction, each of the contiguous sets configurable into different sub-array arrangements, one of the different sub-array arrangements forming parallel sub-arrays with greater extent in the first direction than extent in the second direction;
connecting, in the one of the different sub-array arrangements, sub-arrays between different ones of the contiguous sets with a same number of M in the second direction, the connecting creating a one-dimensional array;
performing ultrasound imaging with the one-dimensional array;
configuring the sub-arrays within each of the contiguous sets so as to provide a multi-dimensional sub-array arrangements as another of the different sub-array arrangements and performing ultrasound imaging of a volume with the other of the different sub-array arrangements, wherein configuring comprises configuring with overlapping L-shaped arrangements across three quadrants for each output in each of the contiguous sets.

8. The method of claim 7, wherein connecting comprises connecting with first switches connectable between the contiguous sets in the first direction.

9. The method of claim 8, wherein each of the contiguous sets has four or fewer outputs connectable with beamformer channels of an ultrasound imager and the first switches connectable between the contiguous sets, and wherein performing comprises receiving signals from the sub-arrays as connected between the different ones of the contiguous sets and providing the signals to the beamformer channels through the outputs of two or more of the contiguous sets.

10. A transducer system for ultrasound imaging, the transducer system comprising:
a two-dimensional array of transducer elements of transducer elements,
a multiplexer configured to connect the transducer elements into a one-dimensional array where each array element of the one-dimensional array has a width of a single one of the transducer elements in azimuth and a height of multiple of the transducer elements in elevation and configured to connect the transducer elements into a multi-dimensional array where each array element of the multi-dimensional array is formed from multiple of the transducer elements, wherein the transducer elements are organized are organized into overlapping L-shaped groups across three quadrants, wherein each transducer element in a respective L-shaped group shares one common connection with the multiplexer with every other element in the respective L-shaped group; and a controller configured to control the multiplexer to form the one-dimensional array or the multi-dimensional array.

11. The transducer system of claim 10, wherein the multiplexer comprises switches where five or fewer of the switches are provided for each of the transducer elements, one of the five or fewer of the switches for connecting between the transducer elements in the one-dimensional array and a remaining four or fewer of the switches for connecting to outputs to beamformer channels of an imaging system.

* * * * *